(12) United States Patent
Tiernan et al.

(10) Patent No.: US 6,579,484 B1
(45) Date of Patent: *Jun. 17, 2003

(54) CO-EXTRUDED TAPER SHAFT

(75) Inventors: Stephen J. Tiernan, Palo Alto, CA (US); Jeong S. Lee, Diamond Bar, CA (US); Mina W. B. Chow, Campbell, CA (US); Stephen G. Schaible, Anaheim, CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/464,932

(22) Filed: Dec. 16, 1999

(51) Int. Cl.[7] ................................. B29C 47/06
(52) U.S. Cl. ........................ 264/173.16; 264/173.16; 264/209.4; 264/209.5
(58) Field of Search ................. 264/173.16, 179.19, 264/209.4, 209.5, 210.1, 210.7, 288.4, 280, 290.2, 294, 296

(56) References Cited

U.S. PATENT DOCUMENTS

| | | |
|---|---|---|
| 3,752,617 A | 8/1973 | Burlis et al. |
| 4,250,072 A | 2/1981 | Flynn |
| 4,282,876 A | 8/1981 | Flynn et al. |
| 4,385,635 A * | 5/1983 | Ruiz ........................ 600/435 |
| 4,888,146 A | 12/1989 | Dandeneau |
| 5,085,649 A | 2/1992 | Flynn |
| 5,099,973 A | 3/1992 | Flotow et al. |
| 5,440,327 A * | 8/1995 | Stevens ........................ 118/50 |
| 5,562,127 A * | 10/1996 | Fanselow et al. ........... 138/137 |
| 5,614,136 A | 3/1997 | Pepin et al. |
| 5,647,127 A * | 7/1997 | Miyata et al. ............... 228/156 |
| 5,725,814 A | 3/1998 | Harris |
| 5,820,594 A * | 10/1998 | Fontirroche et al. ... 604/165.01 |
| 5,830,196 A | 11/1998 | Hicks |
| 5,851,203 A | 12/1998 | van Muiden et al. |
| 5,868,718 A | 2/1999 | Pepin et al. |
| 5,891,110 A | 4/1999 | Larson et al. |
| 6,030,369 A * | 2/2000 | Engelson et al. ........... 604/264 |
| 6,030,371 A * | 2/2000 | Pursley ...................... 427/195 |
| 6,045,547 A | 4/2000 | Ren et al. |
| 6,059,738 A * | 5/2000 | Stoltze et al. ................ 600/585 |
| 6,124,007 A * | 9/2000 | Wang et al. ................. 264/512 |
| 6,143,013 A * | 11/2000 | Samson et al. .............. 604/264 |
| 6,224,803 B1 * | 5/2001 | Tiernan ....................... 264/166 |

FOREIGN PATENT DOCUMENTS

| | | |
|---|---|---|
| DE | 40 32 869 A1 | 4/1992 |
| EP | 0808637 | 11/1997 |
| WO | WO 9638194 | 12/1996 |

\* cited by examiner

*Primary Examiner*—Mark Eashoo
(74) *Attorney, Agent, or Firm*—Blakely, Sokoloff, Taylor & Zafman LLP

(57) ABSTRACT

An apparatus and method for providing a co-extruded, tapered multi-layer shaft. A co-extruded, tapered multi-layer shaft may be fabricated by selecting a first material for the inner layer of the shaft and a second material for the outer layer of the shaft. The first and second materials are then co-extruded by a co-extrusion system including a puller with programmable tapering capabilities. The system forms a hollow tubing having an inner layer and an outer layer, wherein the tubing has the desired tapered characteristics. The result is a tapered tubular shaft having an inner layer and an outer layer.

19 Claims, 6 Drawing Sheets

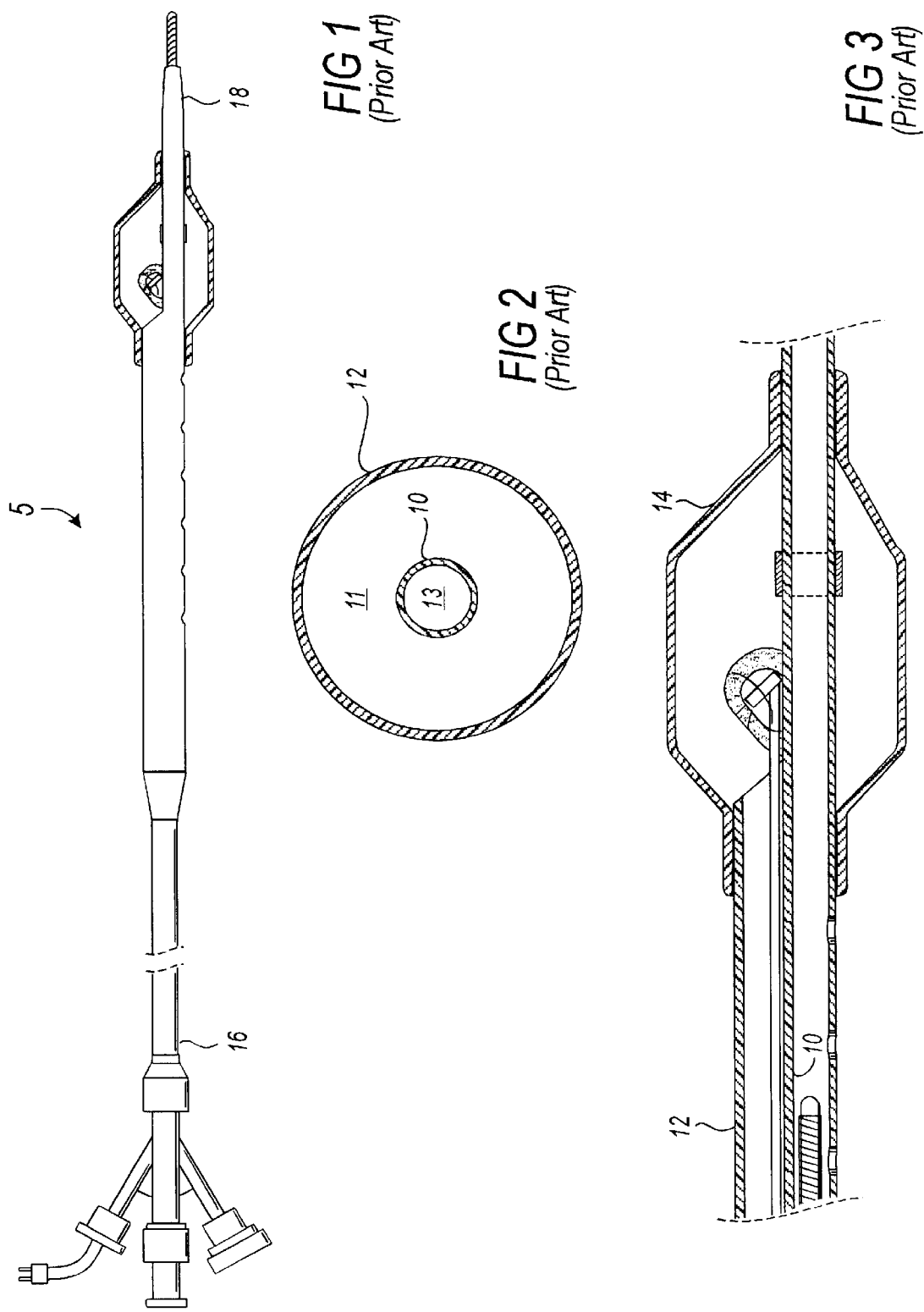

CO-EXTRUDED TAPER SHAFT

BACKGROUND OF THE INVENTION

1. Field of the Invention

This invention relates generally to tubular shafts. More particularly, the present invention involves tapering a co-extruded tubular shaft (e.g., for use in catheters).

2. Description of Related Art

In percutaneous transluminal coronary angioplasty (PTCA), catheters are inserted into the cardiovascular system via the femoral artery under local anesthesia. A pre-shaped guiding catheter is positioned in the coronary artery, and a dilatation catheter having a distensible balloon portion is advanced through the guiding catheter into the branches of the coronary artery until the balloon portion traverses or crosses a stenotic lesion. The balloon portion is then inflated with a fluid to compress the atherosclerosis in a direction generally perpendicular to the wall of the artery, thereby dilating the lumen of the artery. A standard catheter having a relatively constant diameter is difficult to use in some of the smaller arteries and in cases of more advanced stenosis where the artery is closed to such an extent that the catheter cannot be extended through the lesion. Thus, a catheter having a narrowing or a tapered shaft will be beneficial in many circumstances.

A conventional dilatation catheter 5 known in the art for use in treating angioplasty is illustrated in FIG. 1. Typically, dilatation catheters are co-axial catheters having a cross-section such as the one illustrated in FIG. 2. FIG. 3 is a side cross-sectional view of catheter 5 of FIGS. 1 and 2. Catheter 5 has a catheter shaft having an inner member 10 extending through an outer member 12. Typically, outer tubular member 12 is sealed to the proximal shaft of a balloon 14, while inner tubular member 10 is sealed to the distal shaft of balloon 14. Fluid for inflating balloon 14 coupled to the distal end of inner 10 and outer 12 members is introduced through a passageway 11 formed between the tubular members (i.e., the outer lumen). A guide wire (not shown) then passes through a central opening or lumen 13 of inner tubular member 10.

Due to the different responsibilities of each tubular member, inner 10 and outer 12 tubular members generally have different desired material characteristics, which complicates the selection of materials for each of the various catheter components. Typically, outer member 12 is fusion bondable to another catheter component and inner member 10 has a greater lubricity than outer member 12 to allow for ease of passage by the guidewire through inner catheter shaft 13. For example, the material of outer member 12 of the catheter shaft must be selected such that it is compatible with the polymeric material (e.g., polyethylene, terephithelate, polyamide, nylon, etc.) of the catheter component to which it is to be secured (e.g., a balloon or transition piece). Furthermore, because outer member 12 of the catheter shaft is in contact with a patient, the material must be non-traumatic to the lining of the arterial walls into which the catheter is inserted. In contrast, inner member 10 is generally selected for its lubricious properties to allow easier passage of the guide wire through inner lumen 13. Note that the same issues as identified above exist for a catheter shaft having a single tubular member: e.g., the interior of the member should be lubricious and the exterior should be both non-traumatic to the patient and bondable to another catheter component. Thus, when dealing with a single tubular member the material selection is particularly difficult.

One solution for addressing the difficulties in material selection of the more recently developed catheters has been the production of an improved multi-layer member fabricated by a co-extrusion process. A multi-layer member may be used independently as a sheath or as a catheter having a single tubular member (i.e., a single lumen catheter), or in conjunction with a second tubular member to form a co-axial catheter. When used with a co-axial catheter, either or both of the inner and outer tubular members may be a multi-layer member.

A multi-layer member may have many layers or as few as two layers, but typically consists of two to three layers. A cross-sectional illustration of a three layer tubular member 28 is shown in FIG. 4. An inner layer 20 is typically lubricious such that a guidewire or other device may easily be inserted through an interior lumen 26. An outer layer 24 is fabricated from a material that may easily be bonded to another component, e.g., a balloon, and that is strong enough to resist collapse pressure. A middle layer 22 is generally an adhesive or compatibilized polymer used to enhance the integrity of member 28.

The formation of multi-layer tubular member 28 may be achieved through a co-extrusion process using multiple extruders. Generally, the materials selected for each layer are first processed in separate extruders. Each of the selected materials is separately brought to a molten state. Then the materials are brought together to form a single hollow tubing having inner layer 20 from a first material, middle layer 22 from a second material, and outer layer 24 from a third material.

Another complicating factor in the selection of materials for the various components of catheters is the usual requirement that the proximal shaft section (16 of FIG. 1) be much longer and more rigid or stiff than the distal shaft section (18 of FIG. 1) such that proximal shaft section 16 provides pushability to catheter 5. This allows the more flexible distal shaft section 18 to be readily advanced through an often tortuous anatomy. Thus, a stiff proximal shaft may often be joined to a soft distal shaft. Note that the proximal shaft may be made stiffer than the distal shaft due to a larger (i.e., thicker) diameter or through use of a stiffer proximal polymeric tubing made from polymers such as PEEK. The joint between the proximal and distal shafts, however, often makes for an undesirable, abrupt transition between shaft sections.

There are numerous methods of establishing a connection or joint between the stiff proximal shaft and the more flexible distal shaft such as laser powered fusion of polymeric materials. The abrupt transition caused by joining a larger diameter proximal shaft to a smaller diameter distal shaft not only creates a weak point on the catheter shaft at the point of joinder, but the joint region itself is typically stiff and can interfere with the overall flexibility of the catheter shaft. (See transition 30 between a proximal shaft 32 and a distal shaft 34 in FIG. 5). Also, the fluid flow is typically retarded at a transition point 30, which increases the deflation time. Thus, a more gradual tapering of a single catheter shaft would provide several benefits over a catheter shaft having an abrupt transition between the proximal and distal shaft sections.

One solution to providing a tapered catheter shaft has been to "neck down" a small section of a straight shaft, as illustrated in FIG. 6. The straight shaft is submitted to post-process heating (i.e., after the shaft is formed) and then pulled in a controlled manner (i.e., necked down or stretched out). This necking process provides a necked shaft having a tapered appearance, which allows for a more flexible distal section. However, there are several limitations and problems associated with the necking down process. First, the necking down process is usually able to taper only a short section 40 of the shaft. For example, the standard length of the necked down region is approximately 2–10 cm. Thus, if a more gradual taper is desired, for example a taper of the shaft over a longer region (e.g., 1 ft.), a method other than or in addition to necking must be used to taper the shaft. Second, a relatively immediate change (i.e., 3 cm) such as transition 30 illustrated in FIG. 5 can still result at the point of necking (i.e., where the heat is applied), resulting in a weak spot in the catheter. Such weak spots are more susceptible to leaks, kinks and cracks, which adversely affect the reliability of the catheter. Further, the necking process, in addition to reducing the diameter of a short section of the shaft, also results in a stiffer and less desirable shaft.

With multi-layer tubular shafts, the necking process used in the prior art to decrease the diameter of the catheter shaft has several additional and significant disadvantages. For example, outer layer materials are not typically fully compatible with inner layer materials and respond differently to the heat applied during the necking process. Thus, the risk of separation between adjacent layers is increased. In other words, it is often difficult for adjacent layers of a co-extruded multi-layer tubular member to remain bonded during necking as the high strain rate promotes separation of the layers. This is problematic because one layer may "recover" back (i.e., expand when heated and then return to the original size or smaller when cooled). This change to the physical and/or chemical characteristics of the layers of a multi-layer tubular member may cause dimensions of the tubular member to change inconsistently among the various layers or induce broken multi-layer bonds. Because the choice of materials for use in the layers of a multi-layer catheter is already limited, further constraints required by the current necking down process become unduly prohibitive.

Another method of tapering a shaft known in the art is extrusion tapering. Extrusion tapering has several benefits over the above-described necking down process. For example, extrusion tapering may produce a more gradual taper over a longer section of the catheter shaft rather than being limited to a short section of approximately 2–10 cm as with the necking down process. The more gradual taper reduces the occurrence of weak points along the catheter shaft resulting from an abrupt change in shaft diameter. Second, separation is not an issue because the tapering of the shaft is done concurrently with the formation of the tubing itself in the molten state of the polymers, rather than post-process in the solid or transition state of the polymers. Note that extrusion tapering in the prior art has been limited to the fabrication of a tapered single-layer tubular shaft.

A method of providing a multi-layer tube having a gradually tapered shaft is desirable. It is also desirable to replace the necking process using heat with another process that will prevent, or substantially reduce, separation between adjacent layers in a multi-layer tube.

SUMMARY OF THE INVENTION

A tapered, multi-layer tubular shaft and method for manufacturing the same is described. A tapered, multi-layer tubular shaft may be fabricated by selecting at least a first material for an inner layer of the shaft and a second material for an outer layer of the shaft. The materials are then processed through a co-extrusion system comprising a co-extruder system and a taper puller. The co-extruder system forms a hollow tubing with at least an inner layer and an outer layer. The taper puller is used to form at least one segment of the tubing that is tapered. The result is a tubular shaft having an inner and an outer layer with at least one tapered segment.

BRIEF DESCRIPTION OF THE DRAWINGS

The invention is further described by way of example with reference to the accompanying drawings, wherein:

FIG. 1 is a side view of a conventional dilatation catheter known in the art.

FIG. 2 is a front cross-sectional view of a co-axial catheter shaft.

FIG. 3 is a side cross-sectional view of a co-axial catheter shaft.

DETAILED DESCRIPTION OF THE INVENTION

A tapered multi-layer tubular shaft and method for providing the same is described. In the following detailed description, numerous specific details are set forth in order to provide a more thorough understanding of the present invention. However, it will be appreciated that the present invention may be practiced without these specific details. In other instances, well-known devices, methods, procedures, materials, and individual components have not been described in detail so as not to unnecessarily obscure aspects of the present invention. For ease of illustrative purposes only, the present invention is described as used for an inner tubular member of a co-axial catheter. However, other uses, including but not limited to, other tubular shafts, such as single lumen catheters, sheaths, and outer tubular members of co-axial catheters, may also be fabricated using the process described below. With co-axial catheters, either or both of the inner and outer tubular members may be multi-layer and/or tapered.

Figure 4:
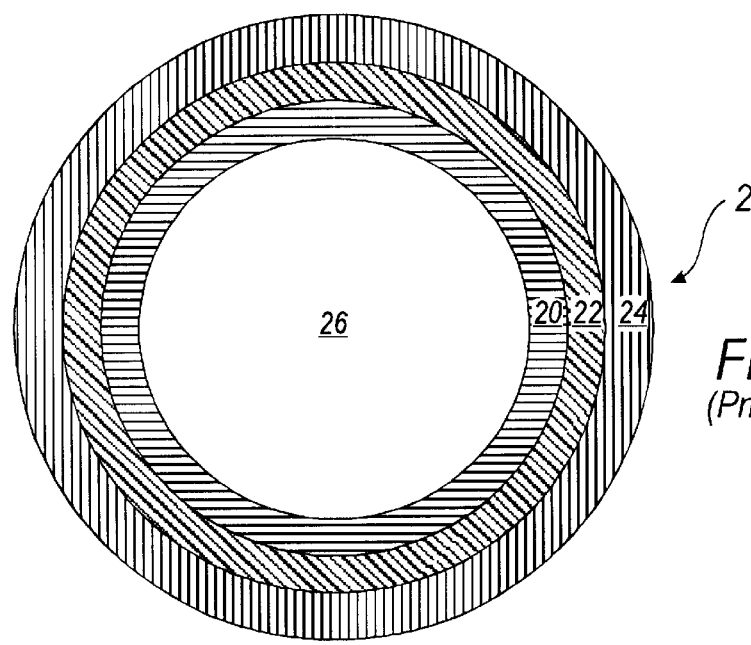
FIG. 4 is a cross-sectional view of a multi-layer tubular member formed by co-extrusion.
Figure 5:
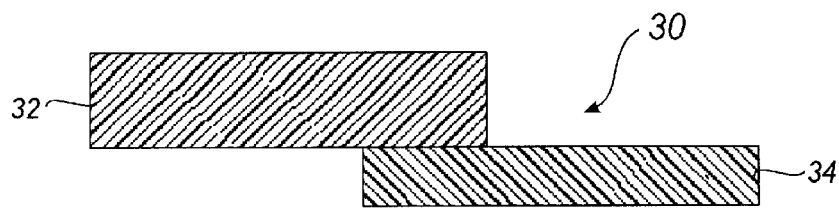
FIG. 5 is a side view of a prior art catheter shaft wherein a stiff proximal shaft is coupled to a flexible distal shaft.
Figure 6:
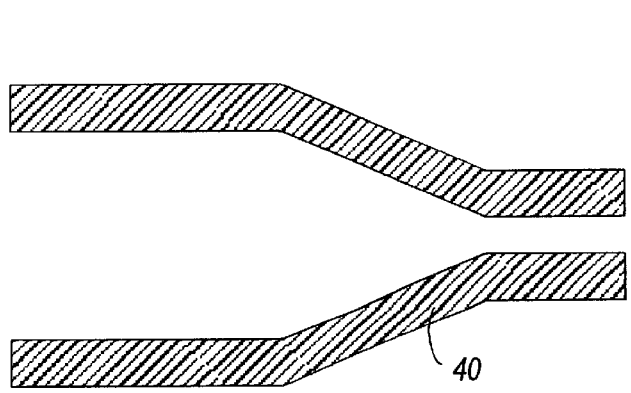
FIG. 6 is a side view of a prior art catheter shaft wherein a section of the shaft has been necked down.

A method for providing a co-extruded multi-layer taper shaft for a catheter is described. The multi-layer shaft of the present invention has at least two layers. A cross-sectional illustration of a three layer shaft 28 is shown in FIG. 4. An inner layer 20 is typically lubricious such that a guidewire or other device may easily be inserted through an interior lumen 26. An outer layer 24 is fabricated from a material that may easily be bonded to another component. A middle layer 22 is generally an adhesive or compatibilizing polymer used to enhance the integrity of shaft 28. The formation of the multi-layer tubular member 28 is achieved through a co-extrusion process performed by an extruder or co-extrusion system having an extruder therein.

In the prior art, catheter shafts are often fabricated by joining a stiff proximal shaft to a smaller diameter flexible distal shaft through use of a joint such as adhesives or a heat fusion process. However, this joint often creates a point of weakness and/or prohibitive stiffness in the catheter shaft. Thus, a gradual rather than an abrupt transition is desired. Tapered shafts of catheters may be fabricated post-process by applying heat to the section of shaft to be tapered, with the heated section then pulled such that it is necked down. This necking or neck tapering method is well-known in the art and will not be described in detail. However, several problems as previously described are associated with both of the above processes.

The present invention addresses these issues by providing a co-extruded, tapered shaft fabricated by tapering a co-extruded multi-layer catheter shaft during extrusion through use of a taper puller rather than by applying heat post-process and then tapering as in the neck tapering process. As will be discussed below in more detail, however, a co-extruded, tapered shaft may be further modified by post-process neck tapering to provide a desirable combination of properties. In this manner, a gradually tapered shaft 50 (see FIG. 7) having a smaller diameter distal end 52 may be produced, wherein the change in the physical properties of inner 54 and outer 56 layers is minimized. Co-extrusion tapering according to the present invention does not limit the selection of materials for the layers of a multi-layer shaft to compatible materials. Furthermore, co-extruded, tapered shaft 50 is not made stiffer as are neck tapered shafts.

Figure 7:
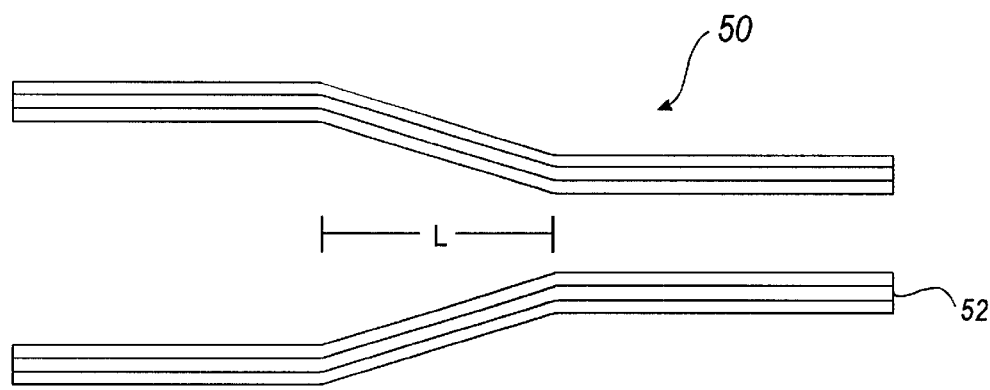
FIG. 7 is a side cross-sectional view of a co-extruded shaft of the present invention wherein a section of the shaft has been tapered during the co-extrusion process to form a tapered shaft.
Figure 9C:
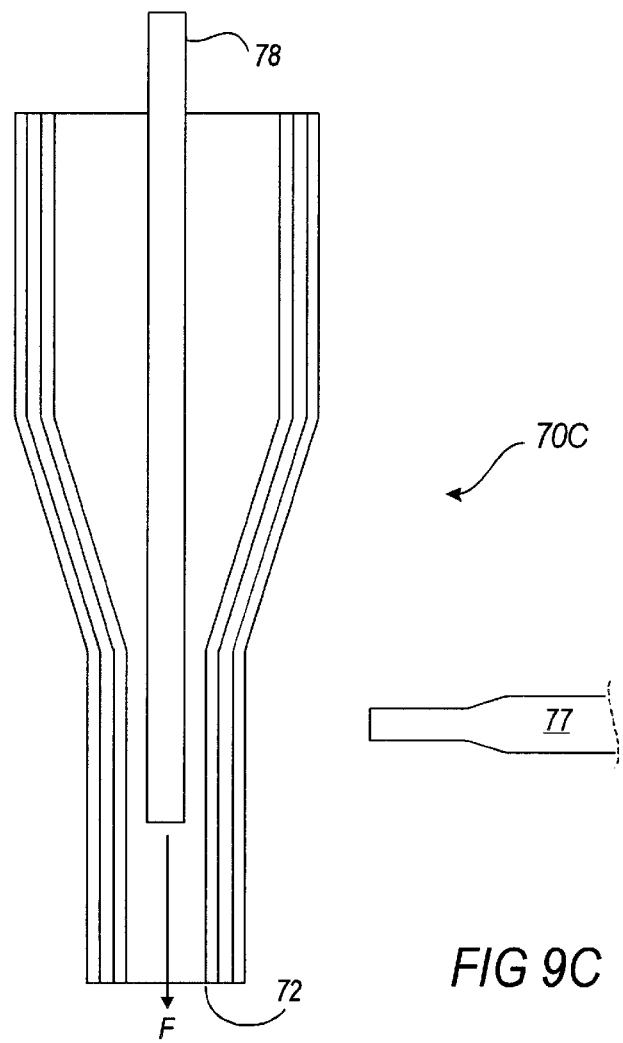
FIG. 9C is a side cross-sectional view of a necking process applied to the tapered shaft illustrated in FIG. 9B.
Figure 8:
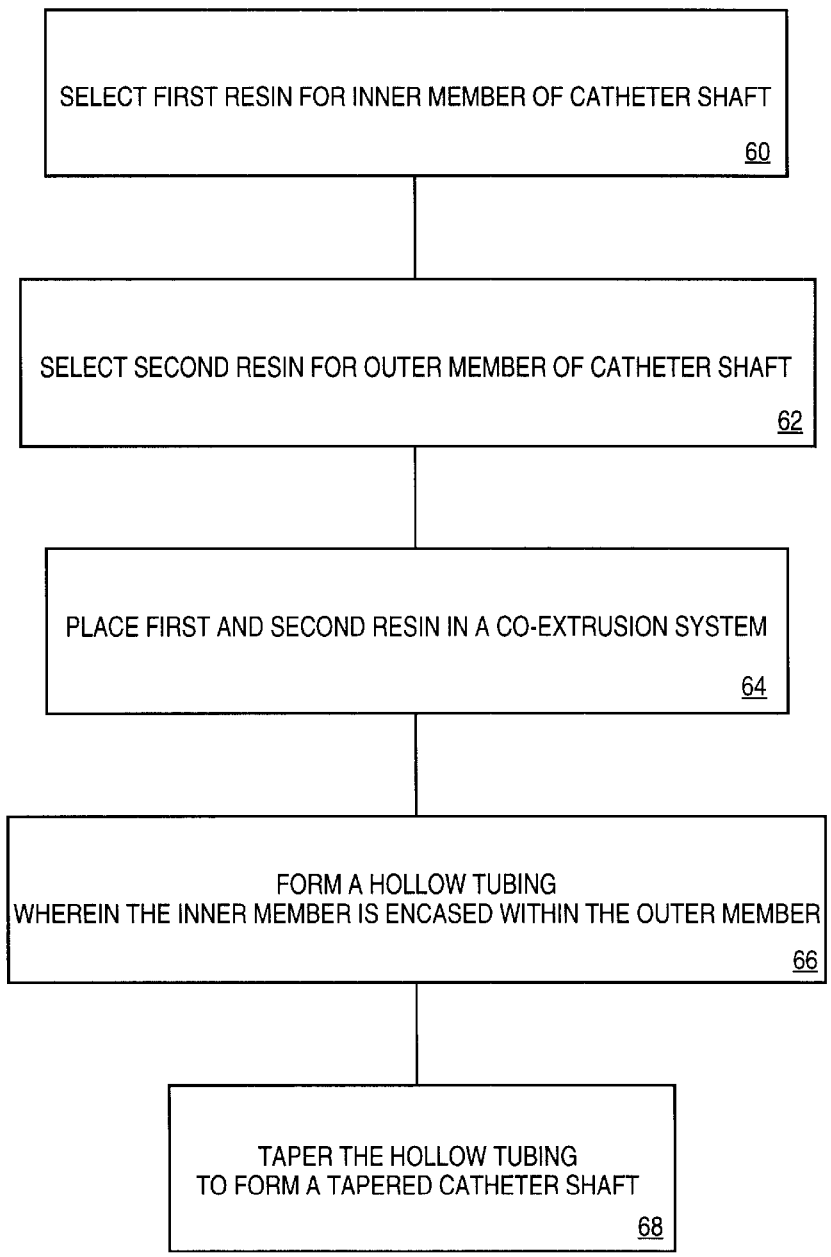
FIG. 8 is a flow chart illustrating the fabrication a co-extruded taper shaft for use as an intraluminal catheter.

FIG. 8 is a flow chart illustrating the fabrication a co-extruded, tapered, multi-layer shaft of the present invention, such as catheter shaft 50 in FIG. 7. In operation 60, a first material or resin for inner layer 54 of the catheter shaft is selected. Recall that the inner layer is typically chosen for its lubricious properties. Possible materials for use in the inner layer include high density polyethylene (HDPE), Polyamides, the Polyetheramide copolymer family, HDPE with and without compatibilizers, low density polyethylene (LDPE), LDPE with and without compatibilizers, linear low density polyethylene (LLDPE), LLDPE with and without compatibilizers, vinyl acetates, urethanes, polyethylene terephthalate (PET), polybutylene terephthalate (PBT), thermoplastic elastomers, isonomers, ethylene acrylic acid polymers, and any combination thereof.

In operation 62, a material or resin for outer layer 56 of the catheter shaft is selected. Considerations to recall when selecting the outer layer material include the fact that material that is non-traumatic to the lining of the arterial wall is preferred, and that the outer layer is typically bonded to another catheter component (e.g., a balloon) and should be compatible with that bonding process. Possible materials for use in the outer layer include materials such as polyamide, polyether block amide, HDPE, low density polyethylene (LDPE), LLDPE, polyethylene copolymers such as ethylene vinyl acetate copolymer (EVA) and ethylene acrylic acid copolymer (EAA), polyurethane, polyesters such as poly-ethylene terephthalate (PET), polybutylene terephthalate (PBT), copolyesters such as Hytrel, other thermoplastic elastomers such as thermoplastic polyolefin (TPO), styrenic thermoplastic elastomers such as C-Flex, and ionomers such as Surlyn.

A third layer 58 (not discussed in the flowchart of FIG. 8) may also be included in the multi-layer catheter shaft 50 of the present invention. Third layer 58 would typically be a middle layer positioned between the first (inner) layer 54 and the second (outer) layer 56. Middle layer 58 is typically an adhesive or compatibilizing polymer such as ethylene acrylic acid copolymer (EAA) or a functionalized polyolefin such as Plexar. It is appreciated that middle layer 58 is not a necessary layer. For example, either inner layer 54 or outer layer 56 may be formed with an adhesive or compatibilizing polymer to eliminate the need for middle layer 58.

Once the materials for inner 54 and outer 56 layers of catheter shaft 50 have been selected, the materials are processed through a co-extrusion system having a co-extruder system and a taper puller, as set forth in operation 64. Extruder systems and taper pullers are known in the art. However, the use of a taper puller is known in the art solely for use with single layer extruded shafts, not for use in fabricating extruded shafts having multiple layers.

The following is a general overview of the tapering process using a taper puller. The operator typically enters/ inputs the desired characteristics of the final shaft profile into the taper puller's control system. Note, however, that the taper puller may also be controlled manually, or commands regarding the final desired characteristics of shaft 50 may be entered concurrently with the co-extrusion process. Such characteristics may include, but are not limited to, specifying an outer diameter and an inner diameter for each of the catheter shaft's layers at both proximal 51 and distal 52 ends of shaft 50 (i.e., specifying the thickness and variation thereof for each layer), and specifying the length (L) of the tapered segment. Note that in this manner not only may the inner diameter of shaft member 50 decrease as the taper is traversed, but the relative thickness of the walls of the inner and outer members may also decrease, and each may even vary independently of each other. Further, the taper puller may be programmed to produce a straight catheter shaft section having a constant inner and outer diameter, followed by a tapered shaft section having a smaller diameter at its distal end, followed by a second straight catheter shaft section, followed by a second tapered shaft section having a smaller diameter at its distal end, etc. Each of these sections may also vary in length.

To form shaft 50, the materials selected for inner 54 and outer 56 layers are initially brought to a molten state, and then co-extruded to form a single hollow tube having outer layer 56 comprising one material and inner layer 54 comprising another material. As part of the co-extrusion process, an air flow may be directed through the hollow tubing to help regulate certain properties or characteristics of the tubing, such as the inner and outer diameters of the hollow tubing.

While multi-layer hollow tubular shaft 50 is being formed, the taper puller concurrently pulls shaft 50 such that it has the desired, pre-programmed characteristics regarding the thicknesses and inner and outer diameters for the different layers and sections of the shaft (operation 68). Note that the change in diameter and thickness may be controlled by the pulling speed of the taper puller, by the amount of air directed through the hollow tubing during formation, and by the flow rate with which each respective molten material is delivered by the extruder. Thus, straight sections may be followed by narrowing sections followed again by straight sections, and the degree or rate of tapering may also be varied.

At this point, co-extruded, tapered, multi-layer shaft 50 is gathered from the co-extrusion system. The co-extruded, tapered, multi-layer shaft 50 produced may have varied dimensions for both inner 54 and outer 56 layers of the catheter shaft 50 throughout the length of the shaft. By producing shaft 50 having varying dimensions throughout the length of the tapered shaft, shaft 50 may gradually change from a stiff proximal segment to a more flexible distal segment. In one embodiment, this also allows the outer, stiffer layer to hold pressure and resist collapse while still allowing the inner, softer layer to prevent kinking of the shaft.

The dimensional tapering during the extrusion process is employed to gradually reduce the dimension of a tube and thereby reduce the flexural modulus of the tapered section. The in-line tapering (drawdown) process produces a bend stiffness value that is lower than most bend stiffness values produced in a post-processing necking operation (cold/post draw). The thinner layers of a co-extruded product in the tapered section also possess greater kink resistance and flexibility than a cold drawn tube, as the degree of axial (machine direction) molecular orientation is lowered.

The embodiment of the present invention discussed above describes the formation of a multi-layer tapered shaft 50 through the use of a co-extrusion tapering process. The resulting multi-layer tapered shaft may then be further modified through post-process necking. The added necking process makes the tapered shaft more pressure resistant and stiffer. Further, it is possible to achieve a higher tolerance with necking. The tighter necking control is possible since the necking of the shaft is being done on a metal core and through a tight tolerance die. Thus, a second embodiment of the invention may consist of tapering a co-extruded multi-layer shaft with a co-extruder system and a taper puller to approximately ¾ of the desired dimension and then necking down to the final desired dimension. This combination of co-extrusion tapering and neck tapering provides finer control over both the dimensions and the stiffness of the tapered shaft. For example, if neck tapering is performed for the entire taper, the shaft is often too stiff and/or has too abrupt a transition. Thus, by using a combination of co-extrusion tapering and neck tapering, finer control may be exerted over the final product's characteristics.

Figure 9A:
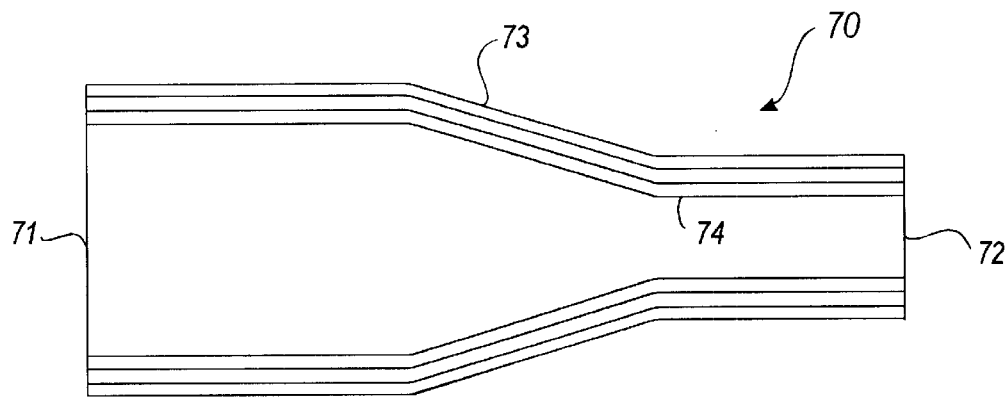
FIG. 9A is a side cross-sectional view of a small balloon dilatation catheter with desired dimensions.

An example of this second embodiment using both co-extrusion tapering and neck tapering is illustrated in FIGS. 9A–9D. FIG. 9A provides a side cross-sectional view of a tapered multi-layer tubular shaft 70 formed by a combination of co-extrusion tapering and neck tapering. In this example, the tubular shaft 70 is a dilatation catheter for use with a small balloon. The inner diameter on the distal end 72 is limited by the balloon deflation time and is approximately 0.01–0.04 in (e.g. 0.027 in), wherein the outer diameter of the distal end 72 is limited by the track performance and the desired small profile to be claimed and is approximately 0.03–0.05 in (e.g., 0.032 in). The outer diameter on the proximal end 71 is approximately 0.02–0.06 in (e.g., 0.0405 in), and the inner diameter on the proximal end is approximately 0.02–0.05 in (e.g., 0.0335 in). The length of the shaft is generally 10–60 in with the narrowing section 73 approximately 5–15 in (e.g., 7 in) and the straight distal section 74 approximately 5–20 in (e.g., 15 in).

Figure 9B:
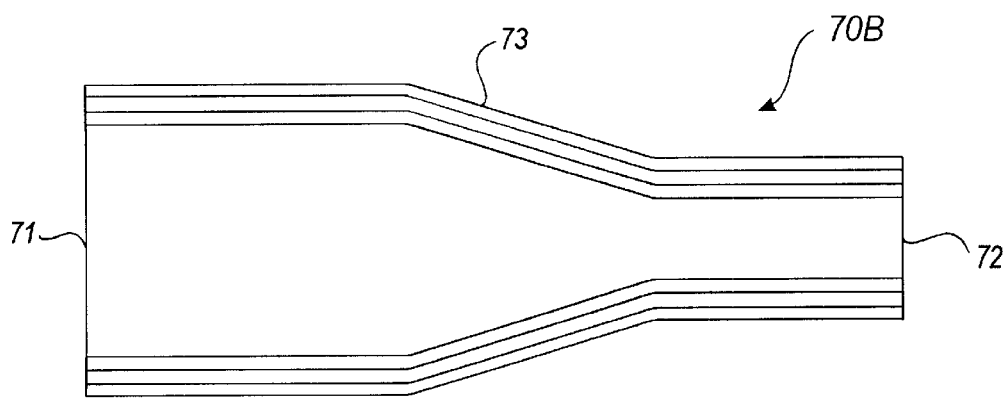
FIG. 9B is a side-cross sectional view of a shaft formed by co-extrusion tapering such that the shaft has only partially been tapered to the final desired characteristics illustrated in FIG. 7.
Figure 9D:
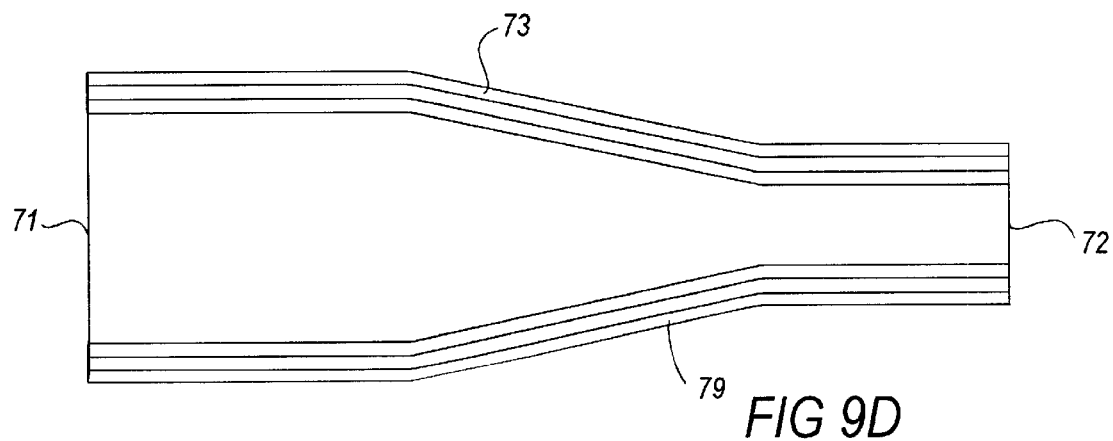
FIG. 9D is a side cross-sectional view of a tapered multi-layered shaft formed by a combination of co-extrusion tapering and neck tapering.

When tested for a particular use at a severe pressure strength, the distal straight section 74 was found to be too weak. Because necking will make the shaft 70 stronger, the shaft 70 is first extruded to an inner diameter of approximately 0.02–0.045 in (e.g., 0.0285 in) and an outer diameter of approximately 0.032–0.04 in (e.g., 0.0345 in) as shown in FIG. 9B (the co-extruded, tapered dimensions are slightly greater than the desired final product dimensions illustrated in FIG. 9A). The co-extruded, tapered shaft 70B is then necked down by a process illustrated in FIG. 9C until the shaft 70B acquires the desired final dimensions detailed above in reference to FIG. 9A. To neck the shaft 70B, a mandrel 78 is inserted into the lumen 76 of the shaft 70B. The shaft 70B is positioned into the necking machine with the distal end 72 pointed down and a weight hung on the distal end 72. A heater nozzle 77 applies heat to the section of the shaft 70B to be necked such that the segment of the shaft 70B distal to the point where heat is applied is necked and forms shaft 70C. In this embodiment, the necking starts approximately 1.5 in from the transition 79 of the tapered section to the distal straight section. After the necking process is complete, the shaft 70C is trimmed to the desired final length as shown in FIG. 9D.

Figure 10:
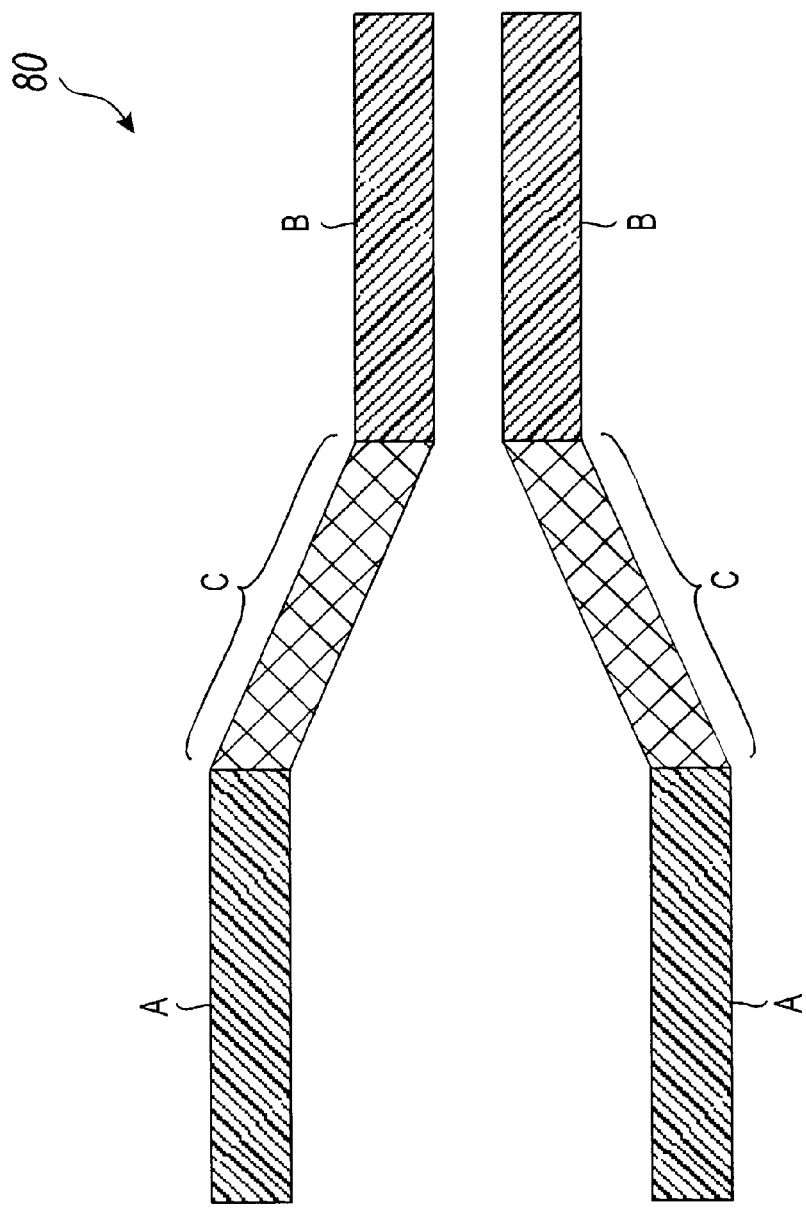
FIG. 10 is a side cross-sectional view of a co-extruded taper shaft having a variable transition.

A third embodiment of the present invention involves tapering a shaft consisting of a variable transition between a first material and a second material. FIG. 10 provides a side cross-sectional view of tapered shaft 80 having a variable transition between materials A and B. Note that the transition between materials may be relatively quick and immediate or may have a longer transitional segment C (as illustrated) that consists of a combination or composite of materials A and B.

A shaft 80 having a variable transition may be formed by an extrusion tapering process using the same taper puller described above. Rather than the first and second materials being tapered and extruded together to form a shaft having multi-layers, this embodiment involves concurrently tapering and extruding a shaft formed by extruding a first material and then a second material to form a single variable layer tubular shaft 80. Note, that a variable transition layer may also be used as one of several layers in a multi-layer tapered shaft.

The present invention provides several advantages over both the separate joint transitions (e.g., fusion) and/or the necking down process used to create tapered shafts in the prior art. Not only does the necking down process often result in separation of adjacent layers of a co-extruded multi-layer shaft, the necking process itself typically makes the shaft stiffer. In contrast, the co-extruded, tapered multi-layer shaft of the present invention is not as stiff along the transition where softness is needed the most.

Note that the present invention increases the overall flexibility of the catheter shaft as the length of the shaft is traversed toward the distal end. The proximal end, however, remains stiff so that the catheter shaft is still pushable and more easily controlled. Moreover, by varying the wall thickness and the dimensions of the inner and outer layers through the length of the co-extruded, tapered tube, the catheter shaft gradually changes from stiff in the proximal segment to more flexible in the distal segment. Further, the co-extruded, tapered shaft also helps to simplify catheter-manufacturing processes by eliminating the need for post-process necking and/or use of transitional joints between proximal and distal segments, while still meeting the same dimensional requirements throughout the catheter.

What is claimed is:

1. A method of fabricating a tapered tubular shaft, comprising:

forming a hollow tubing having an inner layer comprising a first material and an outer layer comprising a second material through a co-extrusion system; and concurrently tapering, through pulling, said inner layer and said outer layer of said hollow tubing while forming said hollow tubing.

2. The method of claim 1 wherein said first material is selected from the group consisting of: high density polyethylene (HDPE), polyamides, the polyetheramide copolymer family, HDPE with and without compatibilizers, low density polyethylene (LDPE), LDPE with and without compatibilizers, linear low density polyethylene (LLDPE), LLDPE with and without compatibilizers, vinyl acetates, urethanes, polyethylene terephthalate (PET), polybutylene terephthalate (PBT), thermoplastic elastomers, ionomers, ethylene acrylic acid polymers, and any combination thereof.

3. The method of claim 1 wherein said second material is selected from the group consisting of: polyether block amide, high density polyethylene (HDPE), low density polyethylene (LDPE), linear low density polyethylene (LLDPE), polyethylene copolymers, ethylene vinyl acetate copolymer (EVA), ethylene acrylic acid copolymer (EAA), polyurethane; polyesters, polyethylene terephthalate (PET), polybutylene terephthalate (PBT), copolyesters, Hytrel; thermoplastic elastomers, thermoplastic polyolefin (TPO), styrenic thermoplastic elastomers, C-Flex, ionomers, Surlyn, and any combination thereof.

4. The method of claim 1 further comprising programming said co-extrusion system for a final desired profile of said hollow tubing.

5. The method of claim 4 wherein programming said co-extrusion system further comprises specifying an inner diameter and an outer diameter for both a proximal and a distal end of said hollow tubing.

6. The method of claim 1 wherein forming said hollow tubing comprises melting said first and second materials.

7. The method of claim 1 wherein forming said hollow tubing further comprises co-extruding said first and second materials to form said hollow tubing having said inner layer and said outer layer.

8. The method of claim 7 wherein tapering said hollow tubing further comprises pulling said tubing to form a tapered hollow tubing, wherein said tapered hollow tubing is substantially stiff in a proximal segment of said tubing and substantially flexible in a distal segment of said tubing.

9. The method of claim 7 wherein tapering said hollow tubing further comprises pulling said tubing to form a tapered hollow tubing, wherein said tapered hollow tubing has a distal diameter smaller than a proximal diameter.

10. The method of claim 1 wherein tapering said hollow tubing further comprises tapering said hollow tubing to form a dilatation catheter shaft.

11. The method of claim 1 further comprising necking said hollow tubing.

12. The method of claim 1 wherein said hollow tubing includes a middle layer comprising a third material.

13. The method of claim 12 wherein said third material is selected from the group consisting of: an adhesive polymer, ethylene acrylic acid copolymer (EAA), functionalized polyolefin, Plexar, and any combination thereof.

14. A method of fabricating a tapered tubular shaft, comprising:
forming a hollow tubing having a distal section and a proximal section through a co-extrusion system, wherein said distal section comprises a first material and said proximal section comprises a second material; and
concurrently tapering, through pulling, said proximal section and said distal section of said hollow tubing to form a narrowing section therebetween while forming said hollow tubing.

15. The method of claim 14 further comprising programming said co-extrusion system for a final desired profile of said hollow tubing.

16. The method of claim 15 wherein programming said co-extrusion system comprises specifying an inner diameter and an outer diameter for both a proximal and a distal end of said hollow tubing.

17. The method of claim 14 further comprising melting said first and second materials.

18. The method of claim 14 wherein forming said hollow tubing further comprises forming a hollow tubing having a first and a second layer, wherein said first layer has a distal section comprising said first material and a proximal section comprising said second material and said second layer comprises a third material.

19. The method of claim 14, wherein tapering said hollow tubing further comprises pulling said tubing to form a tapered hollow tubing.

* * * * *